United States Patent [19]

Marston

[11] Patent Number: 5,046,357

[45] Date of Patent: Sep. 10, 1991

[54] HARDNESS TESTING DIAMOND INDENTER

[75] Inventor: William T. Marston, Milton, Mass.

[73] Assignee: Crafts Precision Industries, Inc., Canton, Mass.

[21] Appl. No.: 467,499

[22] Filed: Jan. 19, 1990

[51] Int. Cl.$^5$ .............................................. G01N 3/42
[52] U.S. Cl. .......................................... 73/85; 29/428
[58] Field of Search ......................... 73/85, 81; 29/428

[56] References Cited

U.S. PATENT DOCUMENTS

| | | | |
|---|---|---|---|
| 1,571,310 | 2/1926 | Wilson | 73/85 |
| 2,216,943 | 10/1940 | Hanemann | 73/85 |
| 2,285,200 | 6/1942 | Gilmore | 73/85 |
| 2,361,441 | 10/1941 | Wilson | 73/85 |
| 2,375,033 | 5/1945 | Parke et al. | 73/85 |
| 2,554,901 | 5/1951 | Fromholt | 73/85 |
| 2,663,185 | 12/1953 | Broschke | 73/85 X |
| 3,738,161 | 6/1973 | Lucke, Jr. et al. | 73/55 |

FOREIGN PATENT DOCUMENTS

| | | | |
|---|---|---|---|
| 622623 | 7/1978 | U.S.S.R. | 73/85 |
| 515140 | of 1939 | United Kingdom | 73/85 |
| 1407714 | 9/1975 | United Kingdom | 73/85 |

*Primary Examiner*—Tom Noland
*Attorney, Agent, or Firm*—James H. Grover

[57] ABSTRACT

An indenter used in hardness testing apparatus to penetrate hard metals and other materials consists of a shank body having at its end a conical frustum with a cylindrical recess extending axially from that end, and a cone of polycrystalline diamond bonded to a hard metal rod which, in turn is bonded in the cylindrical recess concentrically with the axis of the body.

19 Claims, 1 Drawing Sheet

HARDNESS TESTING DIAMOND INDENTER

BACKGROUND OF THE INVENTION

The most common method for testing the hardness of metal and other materials is Rockwell Hardness testing in which hardness of the material is measured by the depth to which it is penetrated under a specified load by the sphero-conical point of a mined natural diamond brazed to the end of a cylindrical metal shank.

The accuracy of the Rockwell testing procedure is dependent in part on the precision with which the conical point of the diamond penetrator or indenter conforms to a standardized shape. The prior standard required that the cone have an included angle of 120° with a tolerance of plus or minus 30 minutes of angle, and currently this tolerance is tightened to 20 minutes for routine production testing, and to 6 minutes for standard laboratory testing. Further the newer standard has tightened the tolerance of the included angle of the diamond cone to plus or minus 20 minutes for indenters used in commercial testing, and to plus or minus 6 minutes for standard laboratory testing.

The standard limiting the 0.200 millimeter radius of the conical tip to a tolerance of plus or minus 0.002 millimeters has been tightened to plus or minus 0.001 millimeters for laboratory testing, although the tolerance for commercial testing remains unchanged.

An additional standard requires that the surface of the cone and the spherical tip shall blend in a truly tangential manner at 500X magnification.

To satisfy the above described standards it is necessary, as a practical matter, that a right, transverse conical section through the tip of the indenter does not deviate from perfect circularity by more than 25 microns in commercial indenters, nor more than 10 microns in laboratory indenters.

With prior indenters it has not been possible to meet the prior standards consistently, and the new standards are less likely to be met. Accordingly it is the object of the present invention to provide a diamond indenter which will not only meet but exceed current standards for Rockwell testing.

SUMMARY OF THE INVENTION

According to the invention an indenter used in hardness testing apparatus for penetrating material under test consists of a cylindrical metal shank with a concentrically cylindrical recess extending axially from a conical end, a cylindrical hard metal rod bonded concentrically in the shank recess, and a cone of polycrystalline diamond bonded to the end of the rod coincident with the conical end of the shank. Preferably the maximum deviation from circularity of a right cross section through the conical tip is 25 microns for commercial indenters, and 10 microns for laboratory indenters. Also the rod is preferably of tungsten carbide.

DRAWING

DESCRIPTION

Figure 2:
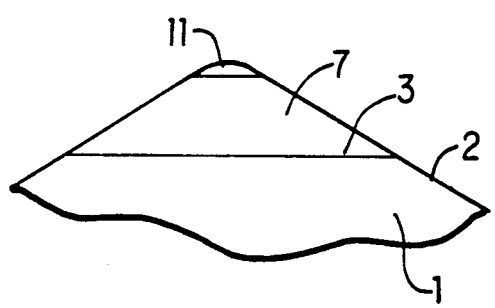
FIG. 2 is an enlarged elevation of the diamond tip.
Figure 3:
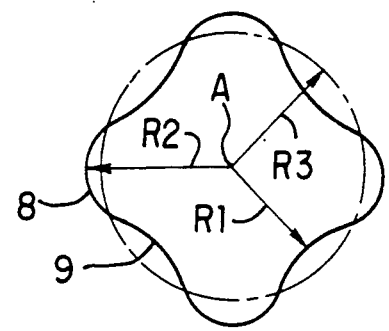
FIG 3 is an end view of the diamond tip.
Figure 1:
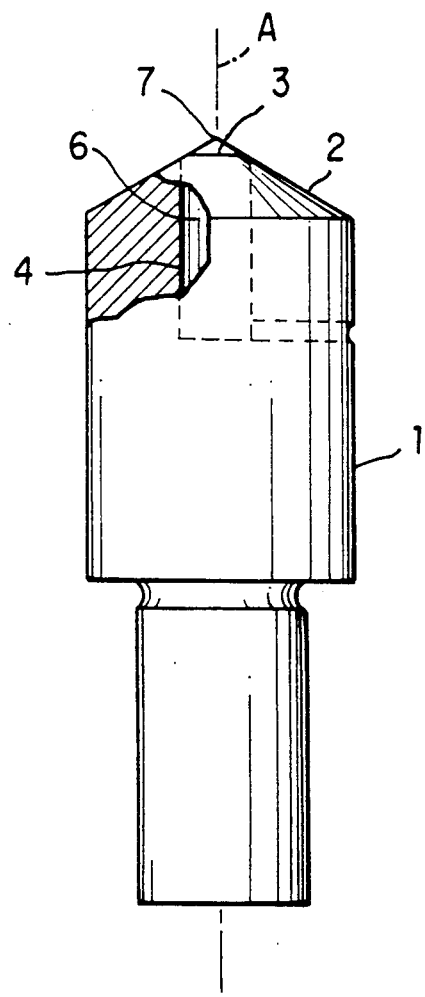
FIG. 1 is a side elevation of an indenter with a conical diamond tip according to the invention.

The diamond indenter in FIG. 1 comprises a cylindrical metal shank body 1, preferably of tungsten carbide, with a 120° frusto-conical end 2 concentric with the axis A of the shank and terminating at a cross section 3. The shank has a cylindrical recess 4 extending axially from its conical end concentrically with its axis. Bonded within the recess is a cylindrical rod of hard metal such as tungsten carbide with a flat end at the plane 3, and with a polycrystalline diamond fused to the flat end. A suitable blank drill rod with a non-conical diamond disk is available from DeBeers Industrial Diamond Division, Ascot, Berkshire, England under the tradename Syndite. According to the invention a drill rod with a polycrystalline diamond is ground to a cone of 120° included angle within a tolerance of 20 minutes plus or minus for routine, commercial hardness testing, and plus or minus 6 minutes for standard hardness testing. The polycrystalline diamond cone is ground to a circularity of cross section shown exaggerated in FIG. 3, wherein R2 is the greatest radius of the cone at a rib 8 in a Talyrond trace, R1 is the least radius of the cone at a flute 9, and R3 is the radius of a theoretical mean circle. The precision achieveable in manufacturing the present indenter is such that a right conical section transverse the axis A of the indenter does not deviate from the theoretical mean circle by more than 25 microns in commercial indenters, nor more than 10 microns in laboratory indenters. The tip of the polycrystalline diamond cone can be, and is, ground and lapped to a sphere tangent to the cone with a radius of 0.200 millimeters plus or minus 0.002 millimeters for commercial testing, and plus or minus 0.001 millimeters for laboratory standard testing, with the radius truly tangent to the cone at 500 X magnification.

Such tolerances as specified above for the present diamond indenter have rarely, if ever, been met in prior indenters, but have been met with indenters according to the present invention. The dimensional precision of the present indenter greatly exceeds that of the prior natural diamond mounted directly on the indenter shank. The life of prior indenters was unpredictable, varying from failure on the first indentation to a million indentations, the indentations varying substantially from specified conical dimensions. With a polycrystalline diamond lacking the hard and soft planes of a natural, mined diamond, and premounted on a tungsten carbide rod bonded in a cylindrical shank recess hundreds of thousands of consistently conical indentation can reliably be repeated.

It should be understood that the present disclosure is for the purpose of illustration only, and that the invention includes all modifications and equivalents falling within the appended claims.

I claim:

1. A hardness testing indenter for penetrating a material under test comprising:
    - a cylindrical metal body having a frusto-conical end and a cone shaped diamond secured concentrically with the body and coincident with its conical end; wherein:
    - the body has a concentrically cylindrical recess extending axially from its conical end;
    - a cylindrical hard metal rod is bonded concentrically in the body recess; and
    - the cone is a polycrystalline diamond bonded to the end of the hard metal rod;
    - whereby the body can be thrust axially on the surface of a material under test so that the diamond cone indents the material to a measurable extent allowing for accurately indicating the hardness of the material.

2. An indenter according to claim 1 wherein the maximum deviation from circularity of a cross section of the diamond cone is twenty five microns or less.

3. An indenter according to claim 2 wherein the diamond cone has a spherical tip with a mean radius substantially within two thousandths of a millimeter or less of a radius of two tenths of a millimeter.

4. An indenter according to claim 1 wherein the maximum deviation from circularity of a cross section of the diamond cone is ten microns or less.

5. An indenter according to claim 1 wherein the diamond cone has a spherical tip with a mean radius substantially within two thousandths of a millimeter or less of a radius of two tenths of a millimeter.

6. An indenter according to claim 1 wherein the hard metal is tungsten carbide.

7. An indenter according to claim 1 wherein the hard metal rod is seated against the inner end of the cylindrical recess in the body.

8. The method of making an indenter according to claim 1 comprising the steps of:
forming the cylindrical recess in the metal body;
bonding the hard metal rod in the recess; and
then grinding the polycrystalline diamond extending from the rod to a cone concentric with the end of the body.

9. The method according to claim 8 wherein the rod is seated against the inner end of the recess in bonding.

10. The method according to claim 8 wherein the diamond cone is ground coincident with the frustum of the shank body.

11. The method according to claim 8 wherein the diamond cone is ground to a cross section deviating from circularity no more than twenty five microns.

12. The method according to claim 11 wherein the deviation is no more than ten microns.

13. The method according to claim 8 wherein the hard metal rod is tungsten carbide.

14. The method according to claim 13 wherein the hard metal rod is seated against the inner end of the body recess.

15. The method according to claim 8 wherein the hard metal rod is seated against the inner end of the body recess.

16. A hardness testing indenter for penetrating a material under test comprising:
a cylindrical metal body having a frusto-conical end; and a cone shaped diamond secured concentrically with the body and coincident with its conical end; wherein:
the body has a concentrically cylindrical recess extending from its conical end;
a cylindrical hard metal rod bonded concentrically in the body recess; and
the cone is a polycrystalline diamond bonded to the end of the hard metal rod; the maximum deviation from circularity of a cross section of the cone being twenty five microns or less;
whereby the body can be thrust axially on the surface of a material under test so that the diamond cone indents the material to a measurable extent allowing for accurately indicating the hardness of the material.

17. An indenter according to claim 16 wherein the maximum deviation from circularity of a cross section of the cone is ten microns or less.

18. The method of manufacturing an indenter for hardness testing comprising:
forming an axial, cylindrical recess extending from a conical frustum at one end of a cylindrical shank body axially into the body;
bonding in the recess a cylindrical rod of hard metal with a cylindrical, polycrystalline diamond bonded to one end of the rod and extending outside the recess at that end; and
grinding the extending diamond to a cone concentric with the end of the shank body.

19. The method according to claim 18 wherein the hard metal rod is seated against the inner end of the body recess in bonding.

* * * * *